(12) United States Patent
Koman

(10) Patent No.: US 8,632,786 B2
(45) Date of Patent: Jan. 21, 2014

(54) DOSE AND LOCALIZATION OF BOTULINUM TOXINS IN SKIN AND MUSCLE

(75) Inventor: L. Andrew Koman, Winston-Salem, NC (US)

(73) Assignee: DT Scimed, LLC, Towson, MD (US)

( * ) Notice: Subject to any disclaimer, the term of this patent is extended or adjusted under 35 U.S.C. 154(b) by 0 days.

(21) Appl. No.: 13/373,395

(22) Filed: Nov. 14, 2011

(65) Prior Publication Data

US 2012/0065143 A1      Mar. 15, 2012

Related U.S. Application Data

(62) Division of application No. 12/588,345, filed on Oct. 13, 2009.

(60) Provisional application No. 61/136,908, filed on Oct. 14, 2008.

(51) Int. Cl.
*A61K 38/16*        (2006.01)

(52) U.S. Cl.
USPC ............ 424/247.1; 424/236.1; 514/17.7

(58) Field of Classification Search
None
See application file for complete search history.

(56) References Cited

U.S. PATENT DOCUMENTS

| | | | | | |
|---|---|---|---|---|---|
| 4,524,065 | A | * | 6/1985 | Pinnell | 424/94.2 |
| 5,183,462 | A | * | 2/1993 | Borodic | 604/506 |
| 5,298,019 | A | * | 3/1994 | Borodic | 604/511 |
| 5,401,243 | A | * | 3/1995 | Borodic | 604/511 |
| 6,395,277 | B1 | * | 5/2002 | Graham | 424/184.1 |
| 6,984,375 | B2 | * | 1/2006 | Holland et al. | 424/9.2 |
| 7,229,605 | B2 | * | 6/2007 | Holland et al. | 424/9.2 |
| 7,238,357 | B2 | * | 7/2007 | Barron | 424/239.1 |
| 8,506,970 | B2 | * | 8/2013 | Koman | 424/239.1 |
| 2002/0054896 | A1 | * | 5/2002 | Studin | 424/401 |
| 2003/0026760 | A1 | * | 2/2003 | Holland et al. | 424/9.2 |
| 2004/0086531 | A1 | * | 5/2004 | Barron | 424/239.1 |
| 2005/0019338 | A1 | * | 1/2005 | Holland et al. | 424/184.1 |
| 2008/0069841 | A1 | * | 3/2008 | Panjwani et al. | 424/239.1 |

OTHER PUBLICATIONS

Banholm, T et al, Pediatric Neurology, vol. 37(4), pp. 263-269, Calf muscle volumne estimates: Implications for Botulinum Toxin Treatment?, 2007.*
Kinnett, DK et al, Botulinum toxin A injections in children:Technique and dosing issues, American Journal of Phys. Med. Rehabil., 2004(83 suppl), pp. S59-S64.*
Carruthers, Alastair et al, 2007, American Society of Dermatologic Surgery, vol. 33, pp. 567-571, A Randomized, Evaluator-Blinded, two Center Study of the Safety and Effect of Volumne on the Diffusion and Efficacy of Botulinum toxin type A in the Treatment of Lateral Orbital Rhytides.*
Willenborg, M et al, 2002, March-April, vol. 22(2), pp. 165-168, Technique for Illiopsoas Ultrasound-Guided Active Electromyography-Directed Botulium A toxin Injection in Cerebral Palsy.*
Shaari, Christopher M e tal, Muscle and Nerve, Sep. 1993, vol. 16, pp. 964-969, Quantifying how location and dose of botulinum toxin injections affect muscle paralysis.*
Hu, Gwo-Chi e tal, Clinical Rehabilitation, vol. 23, pp. 64-71, 2009, Botulinum toxin (Dysport) treatment of the spastic gastrocnemius muscle in children with crebral palsy: a randomized trial comparing two injection volumes.*
Jankovic & Brin, "Therapeutic Uses of Botulinum Toxin", The New England Journal of Medicine, pp. 1186-1194, No. 17, 1991.

* cited by examiner

*Primary Examiner* — Albert Navarro
*Assistant Examiner* — Ginny Portner
(74) *Attorney, Agent, or Firm* — John S. Hale; Gipple & Hale

(57) ABSTRACT

A novel dosing regimen for the administration of botulinum toxin based on the pattern, quantity, and location of neuromuscular junctions in the target tissue. Because the number of neuromuscular junctions in a target tissue remains generally stable throughout life and because the pharmacological effect of botulinum toxin is localized at the neuromuscular junction, dosing efficacy is unaffected by muscle mass, age of the patient, or body weight.

19 Claims, 4 Drawing Sheets

DOSE AND LOCALIZATION OF BOTULINUM TOXINS IN SKIN AND MUSCLE

RELATED APPLICATIONS

This is a divisional application claiming priority from U.S. patent application Ser. No. 12/588,345 filed Oct. 13, 2009 and the benefit of U.S. Provisional Application No. 61/136,908, filed Oct. 14, 2008.

STATEMENT REGARDING FEDERALLY SPONSORED RESEARCH OR DEVELOPMENT

None

REFERENCE TO SEQUENCE LISTING, A TABLE OR A COMPUTER PROGRAM LISTING COMPACT DISC APPENDIX

None.

BACKGROUND OF THE INVENTION

1. Field of Invention

This invention relates to a dosing protocol for the administration of botulinum toxin that maximizes efficacy and specificity while minimizing the likelihood of overdosing and undesirable side effects of botulinum toxin treatment.

2. Background of the Invention

Botulinum toxins, in particular botulinum toxin type A, have been used in the treatment of a number of neuromuscular disorders and conditions involving muscular spasm as well as in cosmetic procedures; for example, strabismus, blepharospasm, spasmodic torticollis (cervical dystonia), oromandibular dystonia and spasmodic dysphonia (laryngeal dystonia). The toxin binds rapidly and strongly to presynaptic cholinergic nerve terminals and inhibits the exocytosis of acetylcholine by decreasing the frequency of acetylcholine release thereby reducing or eliminating the activation of postsynaptic muscles, nerves, or effector tissues. This results in local paralysis and hence relaxation of the muscle afflicted by spasm.

The term botulinum toxin as used herein is a generic term embracing the family of toxins produced by the anaerobic bacterium *Clostridium botulinum* and, to date, seven immunologically distinct toxins have been identified. These have been given the designations A, B, C, D, E, F and G. For further information concerning the properties of the various botulinum toxins, reference is made to the article by Jankovic & Brin, The New England Journal of Medicine, pp 1186-1194, No 17, 1991 and to the review by Charles L Hatheway, Chapter 1 of the book entitled *Botulinum Neurotoxin and Tetanus Toxin* Ed. L. L. Simpson, published by Academic Press Inc. of San Diego Calif. 1989, the disclosures in which are incorporated herein by reference.

The neurotoxic component of botulinum toxin has a molecular weight of about 150 kilodaltons and is believed to comprise a short polypeptide chain of about 50 kD which is considered to be responsible for the toxic properties of the toxin, and a larger polypeptide chain of about 100 kD which is believed to be necessary to enable the toxin to penetrate the nerve. The "short" and "long" chains are linked together by means of disulphide bridges.

Intramuscular injections of botulinum toxin A are generally used to balance muscle forces across joints, to diminish or decrease painful spasticity, to decrease deforming forces through selective motor paralysis, to diminish neuropathic and nociceptive pain, to diminish dystonic contractures, to decrease muscle deformation after injury or surgery, and to diminish sweating. The target organelles contain soluble NSF attachment receptor (SNARE) proteins and neurotransmitter-containing vesicles which require these SNARE proteins for fusion of the vesicle to the cell membrane and release of neurotransmitter. Targets include neuromuscular junctions, sweat glands, vascular beds and nociceptors.

Therapeutic use of these toxins represents a somewhat unique pharmacokinetic profile. In order for toxin to produce its desired action, it must not only be delivered to the target tissue, e.g. muscle (usually by direct injection), but it must also bind to terminal portions of nerves innervating the target tissue (i.e. the neuromuscular junction), and be transported across the presynaptic terminal membrane into the intracellular domain where the active molecule is cleaved from the binding portion of the divalent complex. Then the active molecule must bind irreversibly and enzymatically inactivate molecules in the nerve terminal specific for neurochemical transmission. Thus the toxin molecules are not delivered systemically to distribute throughout the body. The ultimate target is not a specific muscle or organ but rather molecules located in specific nerves which innervate the target tissue within an anatomically defined region of the target tissue or muscle. For example, within skeletal muscle fibers, nerves do not uniformly distribute through the muscle but rather the terminals of the nerves are restricted to a certain region of the muscle. In the case of muscle fibers, prior research has shown that different muscles have different numbers of neuromuscular junctions and the total number of these neuromuscular junctions is not dependent on the mass or volume of the muscle or the individual but rather on other factors such as the function of the muscle fibers.

Current recommendations and dosing regimens are empirical and utilize dosage based upon bodyweight in, for example, the management of cerebral palsy and in orthopaedic uses. With specific regard to its use in children, the use of botulinum toxin in the management of cerebral palsy and in orthopaedic usage is based on the size and weight of the growing child, rather than age, to insure safety since overall toxicity data was based upon units per kilogram of body weight in primates. U.S. Pat. No. 6,395,277 issued 28 May 2002 shows a dosing regimen for the treatment of cerebral palsy, noting that dosing should occur "preferably . . . in the region of the neuromuscular junction" according to "the number of muscle groups requiring treatment, the age and size of the patient." Similar dosing regimens base relative dosages upon the size of muscle.

Historically, dosage recommendations for administration of botulinum toxin has been an imprecise science. Recommendations have been made on the basis of body weight, body surface area, size or volume occupied by a specific muscle, etc. The overreaching goal for each of these therapeutic or cosmetic uses of botulinum toxins is that the toxin be administered in a dosage and volume appropriate to achieving the desired response while remaining localized within the desired specific region of injection. Because the ultimate site of toxin action is nerve junctions within certain regions of the target tissue, over- and under-dosing remains a significant challenge. Administration of too high an absolute dose (total number of toxin molecules relative to the total number of neuromuscular junction targets) or too high a volume of injection might produce adverse reactions related to diffusion of the toxin. Diffusion of the toxin into undesired areas could produce inappropriate paralysis or pathophysiological responses. Too high a dose will produce the desired effect of tissue paralysis but also result in toxin distribution to non targeted tissues thereby causing an unintended loss of physiological function in these regions. Additionally, delivery of supraoptimal toxin doses presents an undesired immunological challenge which may cause reduced effectiveness on subsequent administrations of the toxin. When a large volume of toxin is delivered, it is likely that toxin molecules will diffuse to distant targets resulting in the dilution of the effect of the toxin at the desired target and inappropriately exposing other regions to the toxin. In a large volume dosing scenario, a higher overall dose of toxin would be required at a later time to overcome the dilution effect thus increasing the exposure of other tissues. In these cases where inappropriate doses or volumes are used, not only may patient safety be compromised but the cost of the procedure is increased due to wasted toxin or treatment of unanticipated pharmacological outcomes.

Perhaps the most obvious examples of this inappropriate dosage are delivery of toxin based on body weight to individuals who are at the extremes of weight distribution curves. The toxin acts at the neuromuscular junction and the quantity of the aforementioned junctions does not change proportionately with changes in body mass. Hence, in these cases, individuals with high and low body mass would receive inappropriately high or low doses, respectively.

Various recommendations have demonstrated clinical usefulness but fail to address that 1) the toxin acts at the neuromuscular junction, and 2) the number of neuromuscular junctions varies from muscle to muscle, and 3) the number of neuromuscular junctions tends not to vary as a person ages. Neuromuscular junctions for individual muscles are not directly proportional to muscle mass or volume. Rather, the distribution of neuromuscular junctions varies from muscle to muscle and the number of neuromuscular junctions is affected minimally by age and total body weight. The existing dosage recommendations are clinically efficacious in 50 to 70 percent of patients, namely large toddlers and adolescents, but may underdose infants and small toddlers and overdose heavy children, teenagers, and adults. What is needed are more precise dosing methods to delineate optimal number of units, volume, and injection sites for individual muscles, thereby improving efficacy, minimizing protein antigen load and subsequent antibody formation, and decreasing costs.

SUMMARY OF THE INVENTION

The present invention is a novel dosing method for botulinum toxin based on the number and distribution of neuromuscular junctions in the target muscle. It includes determining the mass of the target muscle, determining the distribution and location of neuromuscular junctions in that muscle, and injecting an appropriate therapeutic dose of botulinum toxin in the vicinity of and according to the quantity of neuromuscular junctions in the muscle. A dosing regimen based on the quantity of neuromuscular junctions in the aforementioned tissue ensures efficacy, while minimizing possible side effects and minimizing cost by ensuring that only that amount of toxin necessary to achieve the desired effect is used.

It is an object of this invention to provide a safe dosing method for botulinum toxins;

It is another object of this invention to provide an efficacious method for dosing botulinum toxins;

It is still another object of this invention to provide a minimally invasive means of dosing botulinum toxins;

It is yet another object of this invention to provide a cost effective dosing method for botulinum toxins; and, It is an object of this invention to provide a simple, easily complied with dosing method for the use of botulinum toxins.

These and other objects, advantages, and novel features of the present invention will become apparent when considered with the teachings contained in the detailed disclosure along with the accompanying drawings.

DESCRIPTION OF THE INVENTION

While the invention is described in connection with certain preferred embodiments, it is not intended that the present invention be so limited. On the contrary, it is intended to cover all alternatives, modifications, and equivalent arrangements as may be included within the spirit and scope of the invention as defined by the appended claims.

The invention is a novel dosing method for botulinum toxin based on the quantity and distribution of neuromuscular junctions in a target tissue. Previous recommendations for dosing were based on, for example, body mass and/or age. In the present invention, therapeutic dosing is based on 1) the quantity and distribution of neuromuscular junctions and 2) the volume of liquid or other carrier material in which that dose is delivered to the target tissue. This results in decreased incidences of under or over-dosing, minimized direct costs of administrating the substance due to the more efficient use of the toxin itself, and minimized indirect costs resulting from the medical costs avoided by eliminating the likelihood of anaphylaxis and immuno-challenge resulting from too high a dose. Ideal dose in units is therefore based upon the number of NSF attachment receptor (SNARE) containing organelles (i.e., neuromuscular junctions to be blocked); the volume or concentration calculated from the muscle mass; and the number of injection sites is dictated by the length and width of the target tissue.

Figure 1:
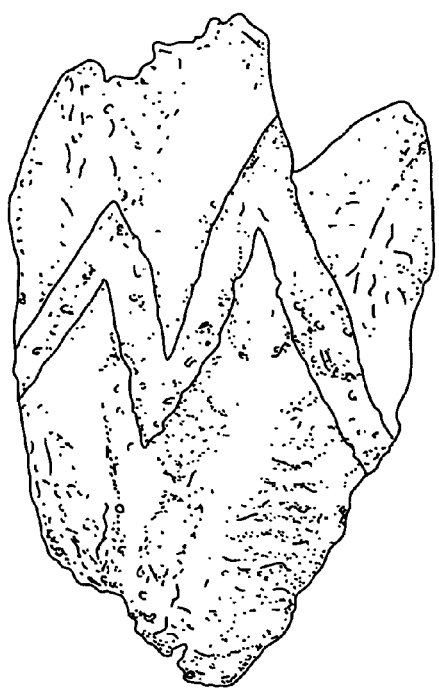
FIG. 1 is a rat gastrocnemius muscle.
Figure 2:
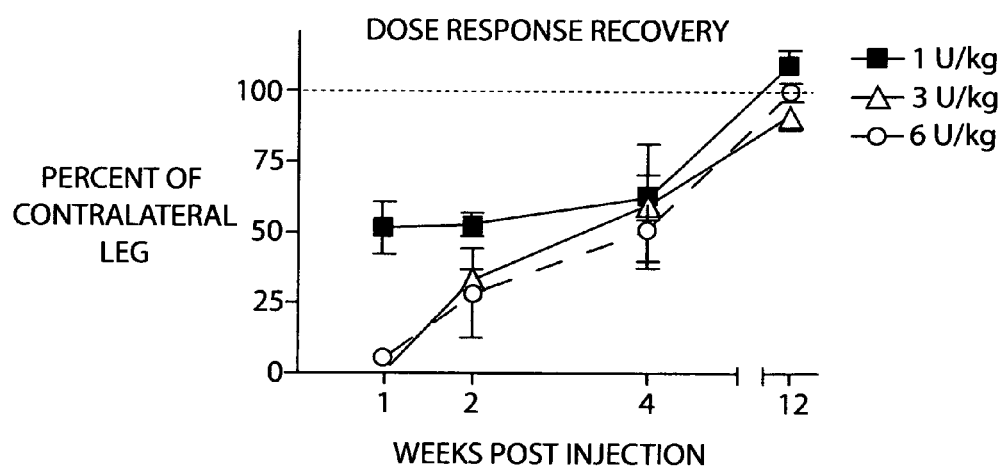
FIG. 2 graphs the dose response recovery of botulinum toxin at dosages of 1 U/kg, 3 U/kg and 6 U/kg.
Figure 3:
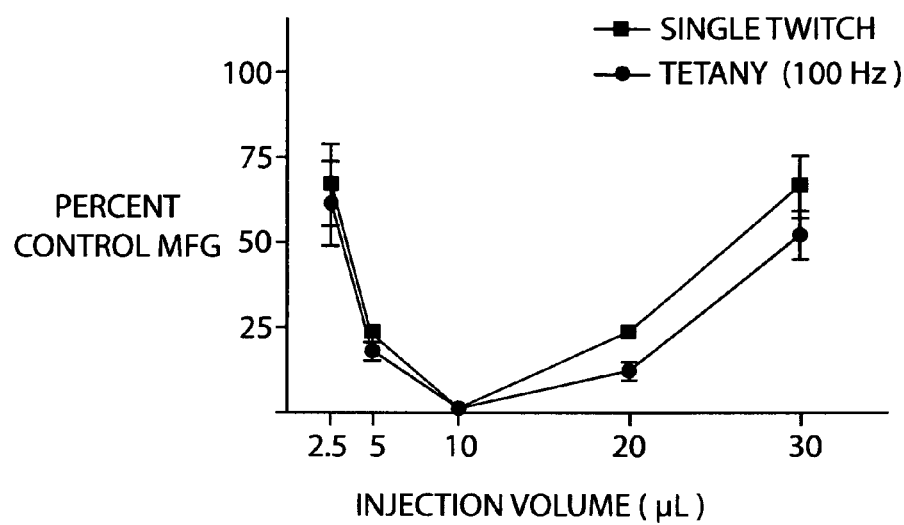
FIG. 3 graphs the effect of different volumes of toxin injection.

As shown in the Dose Response Recovery Graph of FIG. 2, because its efficacy is dependant on the quantity of neuromuscular junctions in the target tissue, dosing of botulinum toxin exhibits clear maximum dosing behavior beyond which an increased dose shows no appreciable change in effect. The neuromuscular junctions of the target tissue are saturated such that additional availability of toxin produces no additional effect. The graph of FIG. 3, however, shows clearly that proper titration of the dose is important. While suboptimal amounts of toxin obviously produce lower degrees of relaxation, supraoptimal doses produce similarly reduced results. It is believed that the reduced results occur because toxin molecules diffuse away from the target site resulting in the dilution of the effect of the toxin at the desired target and inappropriately expose other regions to the toxin. Hence determination of the most efficacious dosage for a target muscle is critical.

Botulinum toxin A is produced by Allergan Pharmaceuticals as BOTOX® and by Ipsen Limited Phannaceuticals as Dysport®. Each vial of BOTOX® contains 100 units of *C. botulinum* type A neurotoxin complex, 0.5 mg of human albumin, and 0.9 mg of sodium chloride as a vacuum-dried frozen powder that requires reconstitution. One unit of BOTOX® is equal to the median intraperitoneal lethal dose (LD50) in Swiss-Webster mice weighing 18 to 20 g. The LD50 for Botox® has been calculated in primates at 39 to 56 units/kg body wt. However, the exact lethal dose in humans is unknown. The calculated human LD50 of 59 units is based on an extrapolation of data. Dysport® clostridium botulinum type A toxin-hemogglutinin complex is available in 500-unit vials. Dysport® units of activity equal 1 mouse LD50 based on their specific assay technique and is sometimes referred to in nanograms, with 1 nanogram equal to 40 units. In the United Kingdom and many other countries, it is approved and labeled for multiple indications, including spasticity of the arm in patients following stroke, dynamic equinus foot deformity due to spasticity in ambulant pediatric cerebral palsy patients, two years of age or older, spasmodic torticollis, blephorospasm, and hemifacial spasm. With regard to cerebral palsy, Dysport® dosing is recommended as "30 units/kg body weight divided between both calf muscles.".

Existing clinical data supports that BOTOX® and Dysport® potencies are different; one BOTOX® unit is equal to 2 to 4 Dysport® units. Units are not interchangeable between companies or toxin types using package guidelines and suggested dilution tables.

Both BOTOX® and Dysport® are reconstituted in injectable physiologic saline prior to intramuscular injection. Both the volume of fluid and number of units of drug must be considered when preparing the toxin for injection. Dosage is defined in absolute terms, based on the number of units per target muscle diluted to volume based on the size of the structure to be injected and quantity and distribution of neuromuscular junctions. The number of units to be injected is calculated by the quantity of neuromuscular junctions to be neutralized, and the volume is determined by the mass of the target muscle, and the number of injection sites by the anatomic distribution of the neuromuscular junctions. Once the appropriate number of active toxin molecules (units) for a given muscle is determined, the dose in units remains constant and the volume and number of injection sites is adjusted based upon growth and anatomy. For example, there are an estimated pikamole of active toxin molecules in 100 units of BOTOX® and an estimated 250,000 neuromuscular junctions in the human biceps brachii. Hence, there are sufficient active toxin molecules to block effectively all neuromuscular junctions of the "target" muscle. The toxin is thereafter injected within the muscle or skin as close to the neuromuscular junctions (or other SNARE-containing organelle) as possible using ultrasonography to localize their position.

Visualization of extremity and trunk muscles is performed reliably using linear probe ultrasonography with a frequency of 5-12 Mhz. For injection localization, linear beam applications better define and delineate the anatomic relationships between muscles, tendons or bones. Higher frequencies are recommended for the localization of the superficial muscles or layers, while lower frequencies may be used for deep structures. The muscles are covered by the epimysium which is the connective tissue that surrounds the entire muscle. The epimysium extends into the muscle to become the perimysium, which divides the fascicle into muscle fibers. The perimysium and the muscular fascicles can be identified because the muscular bundles are hypoechoic (less bright) while the epimysium and perimysium appear as hyperechoic structures. On longitudinal scanning, the fascia is depicted as a fibrillar hyperechoic sheath surrounding the muscle.

There are approximately 250,000 neuromuscular junction in the human biceps brachii muscle. Other human extremity muscles (e.g., the lateral and medial head of the gastrocnemius) have a similar neuromuscular junction density. The total dosage of botulinum toxin (i.e., the absolute number of toxin molecules administered) is given based on the mass of the muscle rather than on the body weight of the individual and injected within 3.0 cm of the area of the muscle containing the neuromuscular junctions (based on ultrasound localization). Thus, for muscles like the soleus where junctions are distributed along the length of muscle fibers, toxin is delivered in multiple locations following the full length of the muscle. In contrast, for muscles like the biceps brachii or medial and lateral head of the gastrocnemius the injection pattern is an inverted U shape following the distribution of the neuromuscular junctions. For example, where 75U is sufficient to produce blockade of the neuromuscular junctions in the lateral gastrocnemius, the biceps brachii has a mass 22% larger than the lateral gastrocnemius, therefore requiring 91U for efficacy. These absolute amounts are then diluted relative to increasing mass and injected adjacent the neuromuscular junctions in the target muscle.

Table 1 shows muscles relative to the lateral gastrocnemius and recommended dosages.

TABLE 1

| Range of Body wt. (kg) | 0-5 | 5-10 | 10-20 | 20-40 |
|---|---|---|---|---|
| Concentration (U/ml) | 100 | 50 | 25 | 12.5 |
| Total U of Botox | 75 | 75 | 75 | 75 |

| muscle | mass relative to lateral gastrocnemius m. | ml per muscle | 2X ml per muscle | 3X ml per muscle | 4-5 X ml per muscle |
|---|---|---|---|---|---|
| lateral gastrocnemius | 1.00 | 0.8 | 1.5 | 2.3 | 3.4 |
| medial gastroc | 1.48 | 1.1 | 2.2 | 3.3 | 5.0 |
| tibialis posterior | 0.84 | 0.6 | 1.3 | 1.9 | 2.8 |
| tibialis anterior | 0.66 | 0.5 | 1.0 | 1.5 | 2.2 |
| soleus | 2.63 | 2.0 | 3.9 | 5.9 | 8.9 |
| FHL | 0.44 | 0.3 | 0.7 | 1.0 | 1.5 |
| Sartorius | 0.56 | 0.4 | 0.8 | 1.3 | 1.9 |
| Semimembranosus | 0.98 | 0.7 | 1.5 | 2.2 | 3.3 |
| Semitendinosus | 0.70 | 0.5 | 1.1 | 1.6 | 2.4 |

TABLE 1-continued

| | | | | | |
|---|---|---|---|---|---|
| Gracilis | 0.32 | 0.2 | 0.5 | 0.7 | 1.1 |
| Pronator Teres | 0.23 | 0.2 | 0.3 | 0.5 | 0.8 |
| Biceps | 1.22 | 0.9 | 1.8 | 2.7 | 4.1 |
| Brachioradialis | 0.39 | 0.3 | 0.6 | 0.9 | 1.3 |
| Pronator Quadratus | 0.07 | 0.1 | 0.1 | 0.2 | 0.2 |
| Supinator | 0.21 | 0.2 | 0.3 | 0.5 | 0.7 |
| FCU | 0.14 | 0.1 | 0.2 | 0.3 | 0.5 |
| FCR | 0.10 | 0.1 | 0.2 | 0.2 | 0.3 |
| FDS | 0.12 | 0.1 | 0.2 | 0.3 | 0.4 |
| FDP | 0.12 | 0.1 | 0.2 | 0.3 | 0.4 |
| ECRB | 0.13 | 0.1 | 0.2 | 0.3 | 0.4 |
| Subscapularis | 1.02 | 0.8 | 1.5 | 2.3 | 3.4 |
| Teres Minor | 0.16 | 0.1 | 0.2 | 0.4 | 0.5 |
| Infraspinatus | 0.76 | 0.6 | 1.1 | 1.7 | 2.6 |
| Supraspinatus | 0.31 | 0.2 | 0.5 | 0.7 | 1.0 |

Table 1 provides a multiplication factor by which the appropriate dosage for other muscles may be determined. For example, the soleus muscle has a mass approximately 2.63 times greater than the lateral gastrocnemius. Where 75U of toxin is efficacious for relaxation of the lateral gastrocnemius, and approximately 0.8 ml of a 100 U/ml concentration of toxin is administered in a patient with a body weight of up to 5 kg, approximately 2.0 ml (i.e., 2.63 times 0.8 ml) is efficacious for relaxation of the soleus. Note that as body weight doubles to 10 kg, 20 kg, and 40 kg, toxin is diluted accordingly but injected in sufficient volume such that the absolute amount of botulinum toxin administered remains the same regardless of muscle size. Increasing muscle mass does not require additional toxin because the number of neuromuscular junctions does not change.

Figure 4:
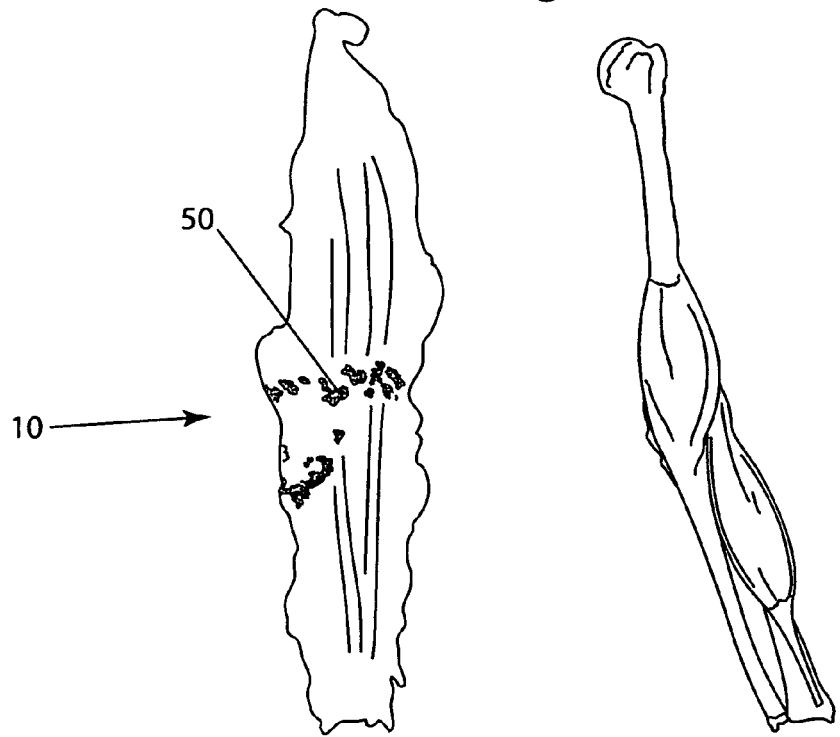
FIG. 4 shows a unipennate muscle with a single transverse band of neuromuscular junctions.
Figure 5:
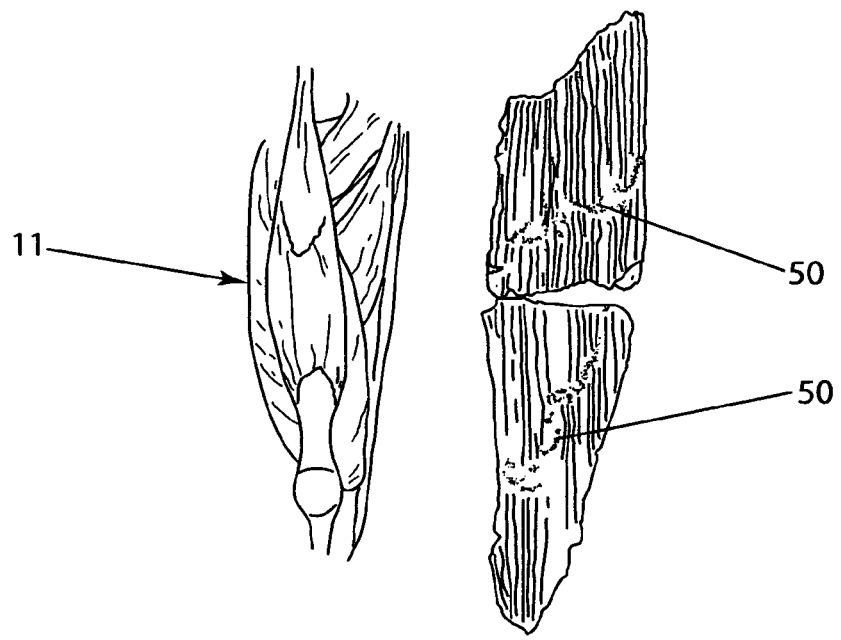
FIG. 5 shows a unipennate gracilis muscle with two transverse bands of neuromuscular junctions.
Figure 6:
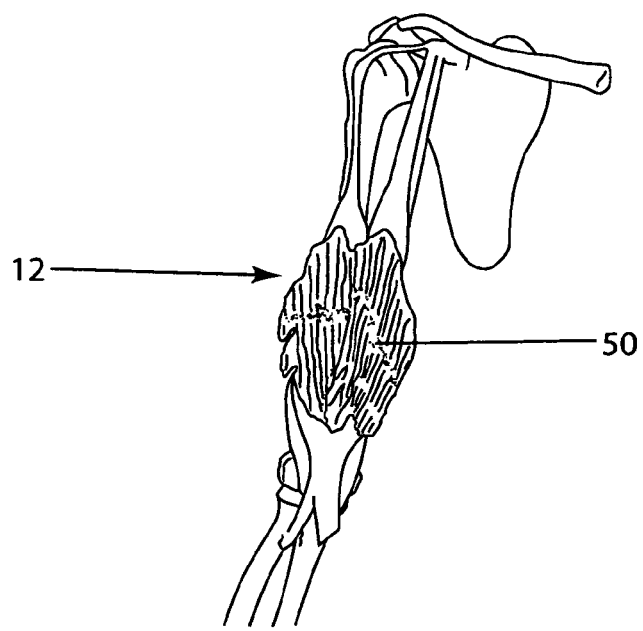
FIG. 6 shows a bipennate converging biceps brachii muscle having neuromuscular junctions located in an inverted "U" shape.
Figure 7:
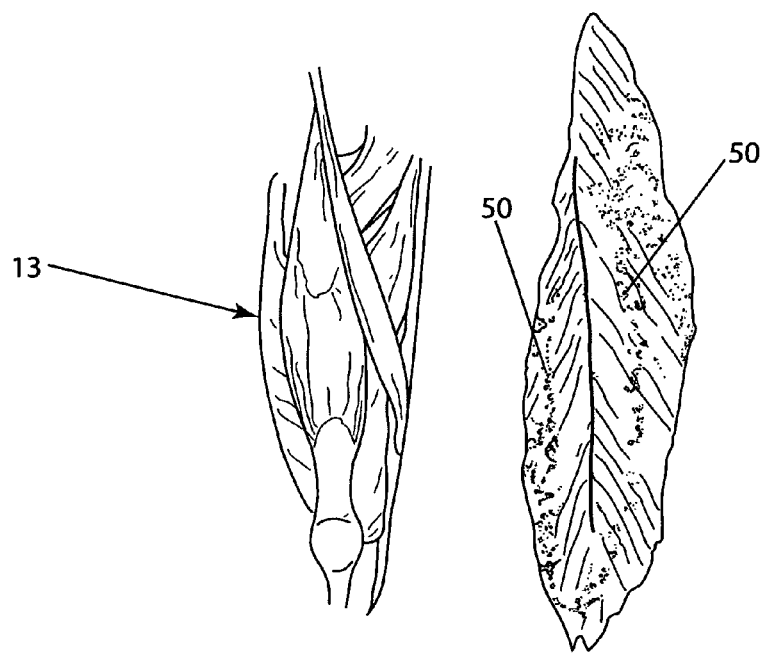
FIG. 7 shows a rectus femoris muscle with two bands of neuromuscular junctions running along its length; and, FIG. 8 shows a deltoid muscle with an irregular pattern of neuromuscular junctions.
Figure 8:
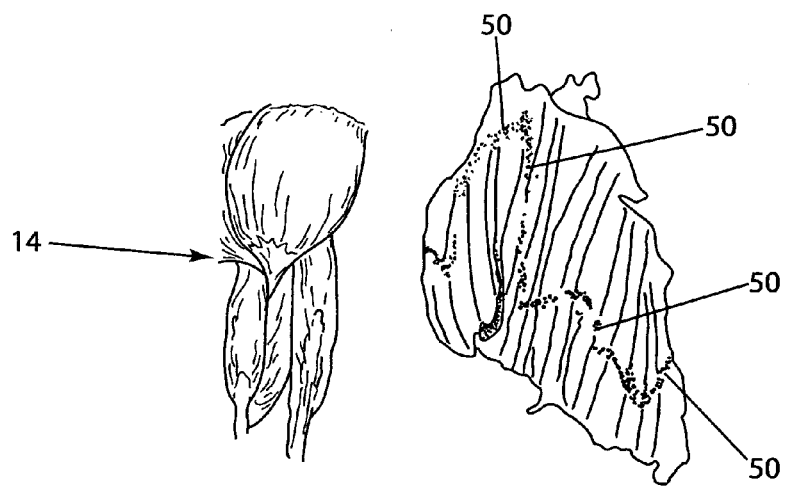

FIG. 4 shows a unipennate muscle 10 with a single transverse band of neuromuscular junctions 50. Intramuscular injection of toxin is most efficacious when delivered within 3.0 cm of this band. Similarly FIG. 5 shows unipennate gracilis muscle 11 with two transverse bands of neuromuscular junctions 50. FIG. 6 shows a bipennate converging biceps brachii muscle 12 having neuromuscular junctions 50 located in an inverted "U" shape. FIG. 7 shows a rectus femoris muscle 13 with two bands of neuromuscular junctions 50 running along its length, and FIG. 8 shows a deltoid muscle 14 with an irregular pattern of neuromuscular junctions 50.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What is claimed is:

1. A method for dosing botulinum toxin in a target muscle of humans who are at the extremes of weight distribution curves with high and low body mass comprising the steps of:
   a) determining the distribution pattern and location of neuromuscular junctions (NMJ) in said target muscle
   b) determining the mass of said target muscle and the absolute amount of botulinum toxin to be used on said target muscle;
   c) diluting a solvated absolute amount of said botulinum toxin so that dilution of the solution by volume increases in an amount proportionate to the mass of said target muscle as a ratio of said target muscle mass in relation to the mass of another base reference muscle with increasing body weight;
   d) injecting doses of said diluted botulinum toxin solution within a range of about 1.0 cm to about 3.0 cm of the area of said target muscle containing said neuromuscular junctions.

2. The method of claim 1 wherein said botulinum toxin is botulinum toxin A.

3. The method of claim 1 wherein said botulinum toxin is botulinum toxin taken from a family of botulinum toxins designated A, B, C, D, E, F and G.

4. The method of claim 1 wherein the location of said neuromuscular junctions of said target muscle is determined using ultrasound localization.

5. The method of claim 1 wherein said target muscle is a unipennate muscle taken from the group consisting of the opponens pollicis, semitendinosus, and brachioradialis, and said neuromuscular junctions are distributed about a transverse midline of said target muscle.

6. The method of claim 1 wherein said target muscle is a unipennate gracilis muscle and said neuromuscular junctions are distributed about two transverse lines on said target muscle.

7. The method of claim 1 wherein said target muscle is a bipennate converging muscle taken from the group consisting of the gastrocnemius and biceps brachii, and said neuromuscular junctions are distributed in a substantially inverted U-shaped pattern on said target muscle.

8. The method of claim 1 wherein said target muscle is a soleus muscle and said neuromuscular junctions are distributed along the length of the muscle fibers.

9. The method of claim 1 wherein said target muscle is a rectus femoris and said neuromuscular junctions are distributed about two longitudinal lines running along the length of said target muscle.

10. The method of claim 1 wherein said target muscle is a deltoid muscle and said neuromuscular junctions are distributed irregularly on said target muscle.

11. The method of claim 1 wherein said base reference muscle is a lateral gastrocnemius.

12. A method for dosing botulinum toxin A in a human target muscle so that toxin distribution to non-targeted tissue is limited comprising the steps of:
   a) determining the mass of said target muscle relative to the mass of a reference muscle;
   b) diluting a solution containing an absolute dose of botulinum toxin A so that dilution of the toxin varies in an amount proportionate with body weight and relative to the ratio of the mass of said reference muscle and the mass of said target muscle;
   c) determining the distribution pattern and location of neuromuscular junctions (NMJ) in said target muscle; and, d) injecting doses of botulinum toxin A diluted solution adjacent said neuromuscular junctions relative to the location and quantity of said neuromuscular junctions in said target muscle to obtain maximum treatment.

13. The method of claim 12 wherein said target muscle is a unipennate muscle taken from the group consisting of the opponens pollicis, semitendinosus, and brachioradialis, and said neuromuscular junctions are distributed about a transverse midline of said target muscle.

14. The method of claim 12 wherein said target muscle is a unipennate gracilis muscle and said neuromuscular junctions are distributed about two transverse lines on said target muscle.

15. The method of claim 12 wherein said target muscle is a bipennate converging muscle taken from the group consisting of the gastrocnemius and biceps brachii, and said neuromuscular junctions are distributed in a substantially inverted U-shaped pattern on said target muscle.

16. The method of claim 12 wherein said target muscle is a soleus muscle and said neuromuscular junctions are distributed along the length of the muscle fibers.

17. The method of claim 12 wherein said target muscle is a rectus femoris and said neuromuscular junctions are distributed about two longitudinal lines running along the length of said target muscle.

18. The method of claim 12 wherein said injected doses of botulinum toxin A are injected within 3.0 cm of said neuromuscular junctions.

19. A method for dosing botulinum toxin in a target muscle of humans comprising the steps of:
   a) selecting a botulinum toxin having maximum effect on said target muscle selected for treatment;
   b) determining the distribution pattern and location of neuromuscular junctions (NMJ) in said target muscle to ascertain the absolute amount of said botulinum toxin to be used on said target muscle through injection sites;
   c) determining the mass of said target muscle;
   d) diluting a solution containing the botulinum toxin so that dilution of the solution by volume increases in an amount proportionate to the mass of said target muscle as a ratio of its mass in relation to the mass of another base reference muscle with increasing human body weight; and
   e) injecting doses of said diluted botulinum toxin diluted solution at locations within 3.0 cm of said neuromuscular junctions of said target muscle in a volume to obtain maximum treatment.

* * * * *